United States Patent
Crooks et al.

(10) Patent No.: US 6,218,434 B1
(45) Date of Patent: Apr. 17, 2001

(54) USE OF THE NATURALLY-OCCURRING QUINONES THYMOQUINONE AND DITHYMOQUINONE AS ANTINEOPLASTIC AND CYTOTOXIC AGENTS

(75) Inventors: Peter A. Crooks; David R. Worthen; Omar A. Ghosheh, all of Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 09/321,832

(22) Filed: May 28, 1999

Related U.S. Application Data

(60) Provisional application No. 60/087,074, filed on May 28, 1998.

(51) Int. Cl.[7] .................................................. A61K 31/115
(52) U.S. Cl. ............................................ 514/690; 514/691
(58) Field of Search ...................................... 514/690, 691

(56) References Cited

U.S. PATENT DOCUMENTS

| | | |
|---|---|---|
| 4,704,384 | 11/1987 | Driscoll et al. . |
| 4,922,901 | 5/1990 | Brooks et al. . |
| 5,482,711 | 1/1996 | Medenica . |
| 5,653,981 | 8/1997 | Medenica . |

OTHER PUBLICATIONS

Johnson et al., Nat. Prod. Lett., 11(4), 241–250 Abstract Only, 1998.*
David R. Worthen et al., "The In Vitro Anti–tumor Activity of Some Crude and Purified Components of Blackseed, Nigella Sativa L., "Anticancer Research, vol. 17, 1997, pp. 1–6.
N.J. Salomi et al., "Antitumour Principles from Nigella sativa seeds," Cancer Letters, vol. 63, 1992, pp. 41–46.
M.J. Salomi et al., "Inhibitory Effects of Nigella sativa and saffron (Crocus sativus) on Chemical Carcinogenesis in Mice," Nutr. Cancer, vol. 16, issue 1, pp. 67–72.
El–Mofty et al., "Prevention of Skin Tumors Induced by 7,12–dimethylbenz (a) anthracene in Mice by Black Seed Oil," Oncology Reports, vol. 4, issue 1, 1997, pp. 139–141.
R. Medenica et al., "Immunomodulatory and Anti–Cancer Activity of Nigella sativa Plant Extract in Humans," Proceedings of the American Association for Cancer Research, vol. 35, Mar. 1994, p. 481.

* cited by examiner

Primary Examiner—Jerome D. Goldberg
(74) Attorney, Agent, or Firm—McDermott, Will & Emery

(57) ABSTRACT

Nigella sativa derivatives, thymoquinone (TM) and dithymoquinone (DIM) are used in treatment of parental and multi-drug resistant human cancers.

8 Claims, 1 Drawing Sheet

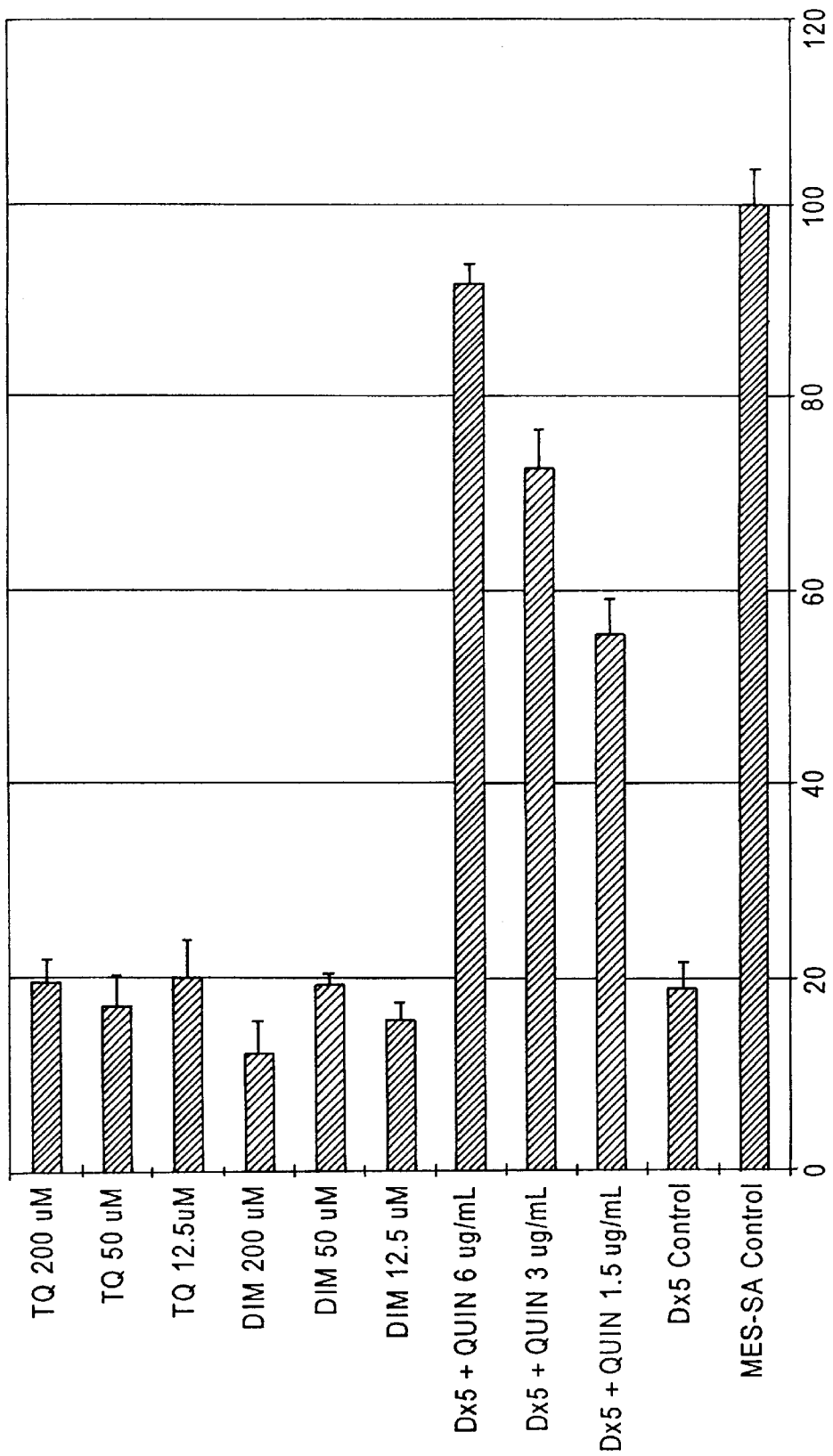

USE OF THE NATURALLY-OCCURRING QUINONES THYMOQUINONE AND DITHYMOQUINONE AS ANTINEOPLASTIC AND CYTOTOXIC AGENTS

CLAIM OF PRIORITY

This application claims priority to Provisional Application Ser. No. 60/087,074, filed May 28, 1998.

FIELD OF THE INVENTION

The present invention relates to the use of Nigella sativa derivatives in the treatment of carcinoma. More specifically, the invention relates to the use of the derivatives thymoquinone (TQ) and dithymoquinone (DIM) in the treatment of parental and multi-drug resistant (MDR) human cancers.

BACKGROUND OF THE INVENTION

Various anti-cancer drugs (a.k.a., antineoplastic agents) are widely used for treatment of both tumorous and leukemic parental cancer cells. Certain cell lines, however, are multi-drug resistant (MDR) and many standard anti-cancer drugs are MDR substrates. MDR, a phenomenon characterized by over-expression of the mdr1 gene product P-glycoprotein and cross-resistance to multiple classes of anticancer drugs, including quinones, seriously complicates and compromises the effective chemotherapy of cancer. For example, as compared to their parental counterparts, many MDR cell lines are over 10-fold more resistant to the well known antineoplastic agents doxorubicin (DOX) and etoposide (ETP). Accordingly, there is a constant search for antineoplastic agents that are not MDR substrates and which are therefore capable of effectively treating MDR cancers.

Naturally occurring substances are a promising source for such agents. Blackseed, the seed of Nigella sativa L. [Ranunculaceae], has been employed for thousands of years as a spice and food preservative, as well as a protective and curative remedy for numerous disorders. The historical tradition of blackseed in medicine is substantial. It is the blackseed referred to by the prophet Mohammed as having healing powers; blackseed is also identified as the curative black cumin in the Holy Bible, and is described as the Melanthion of Hippocrates and Doscorides and as the Gith of Pliny. Several beneficial pharmacological effects have been attributed to various crude and purified components of blackseed, including antihistaminergic, antihypertensive, hypoglycemic, antimicrobial, mast cell stabilizing and anti-inflammatory activities.

Blackseed preparations may have significant in vitro and in vivo antineoplastic activity. A crude methanolic extract of Nigella sativa seed has an in vitro $IC_{50}$ to Erlich ascites carcinoma, Dalton's ascites lymphoma and sarcoma 180 cells of 1.5, 3 and 1.5 µg/mL, respectively, while exerting minimal cytotoxicity to normal lymphocytes. This extract is also active in vivo, completely inhibiting the growth of Erlich ascites carcinoma in mice. Exposure to the volatile oil obtained from blackseed is believed to alter the cellular expression of specific polypeptides in Jurkart T lymphoma cells, suggesting that changes in polypeptide expression might play a role in the biological activities attributed to blackseed. In addition to these direct anti-tumor effects, blackseed preparations may have potential for cancer chemoprevention, as well as for reducing the toxicity of standard antineoplastic drugs. Topical application of a blackseed extract can inhibit the two-stage initiation-promotion (by dimethylbenz[a]anthracene-croton oil) of skin carcinogenesis in mice. Intraperitoneal injections of the same blackseed extract may reduce the incidence of soft tissue sarcomas observed after 30 days of subcutaneous 20-methylcholanthrene (MCA) injections by 67% as compared to MCA-treated controls. Another chemoprotective effect is treatment with a crude ethanolic extract of blackseed, which may significantly reduce cisplatin-induced leukopenia and hemoglobinemia in cisplatin-treated mice.

Although the above applications illustrate the antineoplastic potential of crude blackseed preparations, they do not establish the anti-cancer activity of specific blackseed components, in particular that of the quinones thymoquinone (TQ) and dithymoquinone (DIM). Further, no studies have been reported which evaluate the cytotoxicity of the Nigella sativa seed components TQ and DIM for multi-drug resistant cancer cells. Thus, comprehensive cytotoxicity assays of these potential anticancer drugs in both parental and MDR tumor cell lines are useful for a thorough evaluation and rational therapeutic development of these agents.

SUMMARY OF THE INVENTION

It is accordingly an aspect of the invention to provide methods and compositions for effectively treating both parental and multi-drug resistant cancers.

It is another aspect of the invention to provide methods and compositions, as above, which employ an extract from a natural source.

It is yet another aspect of the invention to provide methods and compositions, as above, which employ an extract from a natural source which is inexpensive and readily available.

These objects and others set forth below are achieved by treating cancer in an individual in need of such treatment by administering to said individual an antineoplastic amount of a compound selected from the group consisting of thymoquinone, dithimoquinone, and mixtures thereof.

To establish antineoplastic and cytotoxic activity, a crude gum, fixed oil and two purified components of Nigella sativa seed, TQ and DIM, were assayed in vitro for their cytotoxicity for several parental and multi-drug resistant (MDR) human tumor cell lines. Although as much as 1% w/v of the gum or oil was devoid of cytotoxicity, both TQ and DIM were cytotoxic for all of the tested cell lines $IC_{50}$'s 78 to 393 µM. Both the parental cell lines and their corresponding MDR variants, over 10-fold more resistant to the standard antineoplastic agents doxorubicin (DOX) and etoposide (ETP), as compared to their respective parental controls, were equally sensitive to TQ and DIM. The inclusion of the competitive MDR modulator quinine in the assay reversed MDR Dx-5 cell resistance to DOX and ETP by 6- to 16-fold, but had no effect on the cytotoxicity of TQ or DIM. Quinine also reduced MDR Dx-5 cell accumulation of the P-glycoprotein substrate $^3$H-taxol in a dose-dependent manner. However, neither TQ nor DIM significantly altered cellular accumulation of $^3$H-taxol. The inclusion of 0.5% v/v of the radical scavenger DMSO in the assay reduced cytotoxicity of DOX by as much as 39%, but did not affect that of TQ or DIM. This suggests that TQ and DIM, which are cytotoxic for several types of human tumor cells, may not be MDR substrates, and that radical generation may not be critical to their cytotoxic activity.

BRIEF DESCRIPTION OF THE DRAWINGS

For a full understanding of the invention, the following detailed description should be read in conjunction with the drawing, which is a bar graph of the effect of serial concentrations of QUIN, TQ and DIM in H-taxol accumulation assays.

DETAILED DESCRIPTION

It has been discovered that the quinones TQ and DIM, two important constituents of *Nigella sativa* seed, are cytotoxic for several types of human tumor cells in vitro. In contrast, neither the fixed oil nor the crude gum preparation obtained from *Nigella sativa* seed exert significant cytotoxic activity for any of the assayed tumor cell lines. Notably, both TQ and DIM are equally cytotoxic for both parental and MDR tumor cells. Their cytotoxicity was not modulated by the presence of 6 μg/mL quinine, a competitive P-gp substrate that reverses MDR cell resistance to DOX and ETP by as much as 16-fold. Further, although serial concentrations of QUIN increase MDR Dx-5 cell uptake of the MDR substrate taxol in a dose-dependent manner, neither TQ nor DIM significantly alter MDR Dx-5 cellular accumulation of taxol. These data suggest that these cytotoxic compounds are not P-glycoprotein substrates. Thus, they can function as useful anticancer drugs, as well as lead compounds for novel agents designed to treat MDR tumors resistant to standard antineoplastics.

The radical scavenger DMSO, employed both experimentally and clinically to reduce the toxicity of radical generating quinones such as DOX, significantly reduced the effective in vitro toxicity of DOX for 4 of the 5 cell lines tested. However, the inclusion of DMSO in the cytotoxicity assays did not modulate the toxicity of TQ or DIM, suggesting that these compounds may exert their cytotoxic effects through mechanisms other than radical generation. This characteristic might be particularly beneficial if these compounds were employed to treat those tumors resistant to standard agents by virtue of their expression of high levels of cellular antioxidants and antioxidant enzymes.

Crude gum and expressed oil preparations from blackseed, as well as the purified quinones TQ and DIM have been evaluated in vitro for their cytotoxicity for the human pancreatic adenocarcinoma cell line CFPAC-1, the human uterine sarcoma cell line MES-SA and its MDR variant, Dx-5, and for the human leukemic cell line K562 and its MDR variant, R7. Both Dx-5 and R7 cells are generally some 25- to 60-fold resistant to various MDR substrates including paclitaxel, Vinca alkaloids and to quinones such as doxorubicin (DOX). These cell lines were chosen in order to evaluate the cytotoxicity of blackseed components for both solid and leukemic tumor cell lines, as well as to evaluate the relative sensitivity of MDR tumor cells to the cytotoxic effects of TQ and DIM. In order to further determine whether or not TQ and DIM are MDR substrates, analogous cytotoxicity experiments were conducted in the presence of quinine (QUIN), a quinoline alkaloid and competitive MDR substrate proven to reverse the MDR defect and significantly increase tumor cell sensitivity to MDR substrates, both in vitro and in vivo. Thus, the effect of QUIN on MDR tumor cell sensitivity to TQ and DIM might further clarify whether or not these blackseed quinones are MDR substrates. An evaluation of the effect of QUIN, TQ and DIM on MDR Dx-5 cellular accumulation of the P-gp substrate $^3$H-taxol was conducted in order to further clarify whether or not TQ and DIM are MDR substrates.

In addition to assaying the cytotoxicity of TQ and DIM for MDR tumor cells, the cytotoxicity of TQ and DIM in the presence of the radical scavenger dimethylsulfoxide (DMSO) was also examined. Concurrent treatment with DMSO reduces the in vitro cytotoxicity of radical-generating quinones such as DOX (21). Thus, the effect, if any, of DMSO on the toxicity of the blackseed components assayed herein is thought to provide insight into the specific mechanisms responsible for their in vitro anti-cancer activity.

The following example illustrates the invention.

EXAMPLE

Materials.

Blackseed (*Nigella sativa* seed) and the expressed oil of blackseed were purchased from Al-Badawin (Cairo, Egypt). Thymoquinone (TQ), ethylenediaminetetraacetic acid (EDTA) and methylthiazoltetrazolium bromide (MTT) were obtained from Sigma (St. Louis, Mo.). HPLC-grade methanol and dimethyl sulfoxide (DMSO) were purchased from Fisher Scientific (Springfield, N.J.). Doxorubicin (Adriamycin, DOX) was purchased from Adria Laboratories (Columbus, Ohio); Etoposide (Vepesid, ETP) was obtained from Bristol Myers Squibb (Princeton, N.J.).

Preparation of blackseed gum and dithymoquinone.

5 g of blackseed were pulverized in a Wiley mill (20 gauge mesh) and stirred in the dark at room temperature for 72 hours in 500 mL methanol. The extract was vacuum-filtered across Whatman No. 1 filter paper (Maidstone, England, UK) and the filtrate concentrated in a rotary evaporator in vacuo at 40° C., leaving 1.1 mL of a clear oil and 0.45 g of a greenish-white gum. The oil was separated from the gum by exhaustive aspiration through a pipette, and the gum was assayed for its cytotoxic activity as described below.

Dithymoquinone (DIM) was prepared by the UV-catalyzed dimerization of TQ and purified by multiple recrystallizations from ethanol, yielding a pale yellow powder. The identity and purity of DIM were verified using $^1$H-NMR, $^{13}$C-NMR, melting point determination and HPLC analysis using well known techniques.

Cell culture.

The human pancreatic adenocarcinoma cell line CFPAC-1, the human uterine sarcoma cell lines MES-SA (parental) and Dx5 (MDR) and human leukemic cell lines K562 (parental) and R7 (MDR) were purchased from ATCC (Rockville, Md.). All cell lines were maintained in McCoy's 5A medium supplemented with 10% newborn calf serum, 100 U/mL penicillin and 100 (μg/mL streptomycin (GIBCO BRL, Grand Island, N.Y.). The cells were cultured in 75 cm$^3$ tissue culture flasks (Dow Corning, Corning, N.Y.) at 37° C. in a humidified atmosphere (5% $CO_2$/95% air) and subcultured at confluence every 3–4 days after detaching adherent cells with 0.4% EDTA in PBS.

MTT cell viability assay.

Cells were plated in 96-well microtiter plates (Dow Corning, Corning, N.Y.) at a density of 1×10$^4$ cells/well in 100 μL media and incubated for 24 hours. The spent media was then carefully and uniformly aspirated from each well with a microtiter pipette and replaced with either 100 μL fresh control media or 100 μL media containing the specified concentration of the tested compounds. Sterile stock solutions of the gum, DOX or ETP dissolved in PBS and filtered through a 0.2 μM filter, and 0.2 M sterile-filtered stock solutions of the fixed oil, TQ or DIM dissolved in methanol were diluted with normal media to prepare the serial concentrations of the various compounds. Control cytotoxicity assays revealed that the highest concentration of methanol used in the studies, 2% v/v, was not toxic for any cell line. After exposure to serial concentrations of the specified compounds for 72 hours, the spent control and drug-containing media were aspirated and 100 μL of fresh media and 100 μL of a solution of 5 mg/mL MTT in PBS were added to each well. The cells were allowed to incubate for 4 hours, the media aspirated, and the blue intracellular formazan product dissolved in 200 μL DMSO. The UV absorbance of each well was immediately determined using a Dynatech MR 580 Microelisa (test wavelength 570 nm/reference wavelength 634 nm). Each cytotoxicity assay was conducted in quadruplicate using two independent experiments. The data were plotted as linear dose-response curves of percent cell viability (UV absorbance) as compared to untreated controls. $IC_{50}$ values are presented as the mean ± SEM as determined by direct extrapolation from the curves.

$^3$H-taxol accumulation studies.

Tritiated taxol accumulation studies were carried out using MDR- MES-SA and MDR+Dx-5 cells. Briefly, 1×10$^6$ cells were grown in 2 mL media in Falcon 35×10 mm sterile tissue culture plates (Becton Dickinson, Lincoln Park, N.J.). After allowing the cells to attach for 24 hours, the spent media was aspirated, and 10 μL of $^3$H-taxol (Amersham Corp., Arlington Heights, Ill.) was added to each well containing either 1 mL of control media or media containing the specified concentration of the indicated compound. After 30 minutes incubation, the assay media was aspirated, the cells washed twice with 1 mL of ice-cold PBS, and the cells lysed for 1 hour with 1 mL of 4% w/v SDS in deionized water. The cell digest was neutralized with glacial acetic acid, and 10 μL aliquots of the lysate were added to scintillation vials containing 10 mL of Ecolite scintillation cocktail (1CN Biomedicals, Irvine, Calif.). Radioactivity was quantified using a Tri Carb C scintillation counter (Packard, Downer's Grove, Ill.). Percent accumulation versus accumulation in non-MDR MES-SA cells was standardized per unit cellular protein present using the bichinconic acid method as described in Gosland, MP et al., Cancer Chemother Parmacol, 37:593–600, 1996, which is hereby incorporated by reference.

Results.

The quinones TQ and DIM inhibited the growth of CFPAC-1 cells in a dose-dependent manner and similarly inhibited the growth of K562, R7, MES-SA and Dx-5 cells. In contrast, neither the fixed oil nor the crude gum preparation demonstrated significant cytotoxic activity to any of the tested cell lines (estimated $IC_{50}$ >10% w/v oil or gum, data not shown). The MDR cell lines Dx-5 and R7 were more than 10-fold resistant to the cytotoxic effects of DOX and ETP as compared to their respective parental controls, MES-SA and K562. However, both the parental and MDR variants of these cell lines were sensitive to the cytotoxic effects of TQ and DIM. Notable, MDR Dx-5 cells, though 10- to 16-fold resistant to DOX and ETP as compared to their MDR-negative parental cell line MES-SA, were almost twice as sensitive to DIM as were the MES-SA cells. The estimated $IC_{50}$'s of the assayed compounds in each cell line are summarized in the following table.

TABLE

| Drug | CFPAC-1 | K5A2 | R7 | MES-SA | Dx-5 |
|---|---|---|---|---|---|
| DOX | 8.48 ± 0.26 | 0.64 ± 0.01 | 9.94 ± 0.4 | 0.89 ± 0.05 | 8.05 ± 0.41 |
| DOX + DMSO | 8.24 ± 0.18 | 0.76 ± 0.05$^b$ | 12.1 ± 0.5$^b$ | 1.48 ± 0.06$^b$ | 12.5 ± 0.45$^b$ |
| DOX + QUIN |  | 0.68 ± 0.02 | 0.64 ± 0.03$^c$ | 0.72 ± 0.02 | 0.58 ± 0.02$^c$ |
| ETP |  | 0.39 ± 0.01 | 15.3 ± 0.40 | 0.33 ± 0.01 | 4.47 ± 0.26 |
| ETP + QUIN |  | 0.39 ± 0.02 | 2.95 ± 0.10$^c$ | 0.36 ± 0.01 | 0.56 ± 0.02$^6$ |
| TQ | 206 ± 8.5 | 275 ± 15.1 | 235 ± 10.9 | 188 ± 9.8 | 255 ± 9.4 |
| TQ + DMSO | 234 ± 12.2 | 250 ± 13.3 | 232 ± 9.9 | 156 ± 8.9 | 232 ± 13.8 |
| TQ + QUIN |  | 300 ± 13.2 | 265 ± 10.4 | 191 ± 8.8 | 243 ± 16.2 |
| DIM | 386 ± 18.5 | 277 ± 8.9 | 225 ± 8.5 | 143 ± 8.7 | 87 ± 2.8 |
| DIM + DMSO | 393 ± 15.3 | 247 ± 13.6 | 160 ± 7.5 | 143 ± 6.9 | 78 ± 4.1 |
| DIM + QUIN |  | 194 ± 12.0 | 161 ± 5.8 | 147 ± 5.2 | 80 ± 3.3 |

As measured by effective $IC_{50}$, the inclusion of 6 μg/mL of the competitive P-gp substrate QUIN in analogous cytotoxicity assays reversed MDR R7 tumor cell resistance to DOX by 15-fold and R7 resistance to ETP by 6-fold (Table I). A similar effect was observed in MDR Dx-5 cells. In the presence of 6 μg/mL free QUIN, Dx-5 resistance to DOX was reduced by 16-fold, and resistance to ETP by 7-fold. In contrast, free QUIN in the assay media did not significantly alter Dx-5 or R7 cell sensitivity to TQ or DIM. These data indicate that TQ and DIM are equally cytotoxic for both parental and MDR tumor cells, and suggest that these two quinones may not be P-gp substrates. Control cytotoxicity assays revealed that 6 μg/mL QUIN was not toxic to any cell line tested.

The effect of including serial concentrations of QUIN, TQ or DIM in the $^3$H-taxol accumulation assays is illustrated in the Figure. MDR Dx-5 cells accumulated only about 20% as much taxol as compared to non-MDR MES-SA parental cells. The presence of the competitive P-gp blocker QUIN in the uptake media reduced taxol accumulation significantly and in a dose-dependent manner. However, neither TQ nor DIM reversed the accumulation defect in Dx-5 cells. Concentrations of these quinones as high as 200 μM did no significantly alter cellular accumulation of taxol.

The inclusion of 0.2% v/v of the radical scavenger DMSO in culture media reduces the cytotoxicity of the quinone DOX to human ovarian tumor cells by as much as 39%. Radiolabelled uptake experiments reveal that this cytoprotective effect is not due to a DMSO-mediated decrease in cellular accumulation of DOX. In order to assess the effect of DMSO on the cytotoxicity of the quinones TQ and DIM, the previously described cytotoxicity assays were repeated in media containing 0.5% v/v DMSO. Although the addition of 0.5% v/v DMSO did not significantly alter DOX cytotoxicity to CFPAC-1 cells, DMSO reduced the cytotoxicity of DOX to K562, R7, MES-SA and Dx-5 cells by 18%, 33%, 39%, and 22%, respectively (Table I). Interestingly, the cytotoxicity of TQ and DIM for the various cell lines examined was not significantly altered when DMSO was included in the assay media. Although the cytotoxic effects of quinones such as TQ and DIM could be attributed to a number of mechanisms, including adduct formation with nucleophilic residues, the failure of DMSO to modulate their cytotoxicity in these experiments suggests that radical formation may be less important to the in vitro cytotoxicity of TQ and DIM than are other mechanisms. Control cytotoxicity assays reveal that 0.5% v/v DMSO was not cytotoxic for any of the tested cell lines.

The pharmaceutical compositions of the present invention can also include various other components as additives or adjuncts. Exemplary pharmaceutically acceptable components or adjuncts which are employed in relevant circumstances include antioxidants, free radical scavenging agents, peptides, growth factors antibiotics, bacteriostatic agents, immunosuppressives, buffering agents, anti-inflammatory agents, anti-pyretics, time release binders, anaesthetics, steroids and corticosteroids. Such components can provide additional therapeutic benefit, act to affect the therapeutic action of the pharmaceutical composition, or act towards preventing any potential side effects which may be posed as a result of administration of the pharmaceutical composition. In certain circumstances, a compound of the present invention can be employed as part of a pharmaceutical composition with other compounds intended to prevent or treat a particular disorder.

The manner in which the compounds are administered can vary. The compounds can be administered by inhalation (e.g., in the form of an aerosol either nasally or using delivery articles of the type set forth in U.S. Pat. No. 4,922,901 to Brooks et al.); topically (e.g., in lotion form); orally (e.g., in liquid form w.

Within a solvent such as an aqueous or non-aqueous liquid, or within a solid carrier; intravenously (e.g., within a dextrose or saline solution); as an infusion or injection (e.g., as a suspension or as an emulsion in a pharmaceutically acceptable liquid or mixture of liquids); or transdermally (e.g., using a transdermal patch). Although it is possible to administer the compounds in the form of a bulk active chemical, it is preferred to present each compound in the form of a pharmaceutical composition or formulation for efficient and effective administration. Exemplary methods for administering such compounds will be apparent to the skilled artisan. For example, the compounds can be administered in the form of a tablet, a hard gelatin capsule or as a time release capsule. As another example, the compounds can be delivered transdermally using the types of patch technologies available from Novartis and Alza Corporation. The administration of the pharmaceutical compositions of the present invention can be intermittent, or at a gradual, continuous, constant or controlled rate to a warm-blooded animal, (e.g., a mammal such as a mouse, rat, cat, rabbit, dog, pig, cow, or monkey); but advantageously is preferably administered to a human being. In addition, the time of day and the number of times per day that the pharmaceutical formulation is administered can vary. Administration preferably is such that the active ingredients of the pharmaceutical formulation interact with target site within the body of the subject.

In general, the invention includes the use of *Nigella sativa* components, including TQ, DIM and mixtures thereof, as well as all derivatives, congeners and analogues thereof, for the palliation or treatment of solid and/or leukemic tumors in animals and/or humans when administered by any or all routes of administration including, but not limited to, the intravenous, intramuscular, intrathecal, intraperitoneal, intralesional, subcutaneous, intradermal, transdermal, intranasal, topical, oral, buccal, rectal, vaginal, intrapulmonary and inhalation routes of administration.

The amount of TQ, DIM or mixture thereof that is used in treatment varies with the size and species of the mammal, the type of cancer, and the method of administration. Generally, the amount of active compound can vary from about 10–500 mg/kg body weight per day, and preferably from about 10–30 mg/kg body weight per day. The administration can be as a single dose or one or more doses administered over a 24-hour period. Injections are preferably in the form of dilute solutions (e.g. 10–50% v/v) and can be effective in the treatment of tumors and leukemias.

For topical administration used in the treatment of skin cancer, a dilute solution (10–50% v/v) may be used in a suitable corner and applied from 1 to 3 times daily to the affected area for a period of from 30 days to 6 months.

The invention also includes the use of *Nigella sativa* components, including TQ, DIM and mixtures thereof, as well as all derivatives, congeners and analogues thereof, for the palliation and/or treatment of solid and/or leukemic tumors when administered orally in a suitable dosage form including, but not limited to, the neat compound(s), or any solution, elixir, syrup, tablet, capsule, suspension, emulsion, microemulsion or adsorption product containing said compound(s) and intended for their oral delivery, in the general dosage range of 1 to 80 mg compound(s)/kg body weight, when administered in single or divided doses during a period of therapy of 1 to 60 days daily, every few days, weekly or monthly as deemed appropriate for therapy by a qualified practitioner of the art.

One skilled in the art can monitor the progress of treatment and adjust the length or dose of active ingredient accordingly.

What is claimed is:

1. A method for treating cancer in an individual in need of such treatment, comprising administering to said individual an antineoplastic amount of a compound selected from the group consisting of thymoquinone, dithymoquinone, and mixtures thereof and wherein the cancer is sensitive the compound.

2. The method as claimed in claim 1, wherein said cancer is multi-drug resistant.

3. The method as claimed in claim 2, wherein the multi-drug resistant cancer comprises a human leukemia.

4. The method as claimed in claim 1, wherein the cancer is selected from the group consisting of human pancreatic adenocarcinoma and human uterine sarcoma.

5. The method according to claim 1, wherein said cancer is sarcoma, carcinoma or leukemia.

6. The method according to claim 5, wherein said sarcoma, carcinoma or leukemia is multi-drug resistant.

7. The method according to claims 5, wherein said carcinoma is adenocarcinoma.

8. The method according to claim 5, wherein said sarcoma or carcinoma is pancreatic adenocarcinoma or uterine sarcoma.

* * * * *